United States Patent [19]

Humphries et al.

[11] Patent Number: 4,704,353
[45] Date of Patent: Nov. 3, 1987

[54] PHOTORESPONSIVE REDOX DETECTION AND DISCRIMINATION

[75] Inventors: Gillian M. K. Humphries, Los Altos, Calif.; John W. Parce, Winston-Salem, N.C.; Harden M. McConnell, Stanford, Calif.

[73] Assignee: Molecular Devices Corporation, Palo Alto, Calif.

[21] Appl. No.: 604,800

[22] Filed: Apr. 27, 1984

[51] Int. Cl.⁴ .................... G01N 33/50; G01N 33/53; G01N 27/30; G01N 27/52

[52] U.S. Cl. ..................... 435/4; 204/1 T; 204/403; 204/412; 324/71.5; 435/7; 435/25; 435/26; 435/28; 436/84; 436/501; 436/805; 436/806; 436/807; 436/827; 436/904

[58] Field of Search ............ 204/1 T, 403, 412; 324/71.5; 435/7, 25, 26, 28; 436/84, 501, 805, 806, 807, 827, 904

[56] References Cited

U.S. PATENT DOCUMENTS

| 4,020,830 | 5/1977 | Johnson | 204/403 X |
| 4,238,757 | 12/1980 | Schenck | 436/806 X |
| 4,486,272 | 12/1984 | Fujihira | 204/1 T |
| 4,562,157 | 12/1985 | Lowe | 436/806 |
| 4,591,550 | 5/1986 | Hafeman | 436/501 |

Primary Examiner—Sidney Marantz
Attorney, Agent, or Firm—Bertram I. Rowland

[57] ABSTRACT

Devices and methods are provided for making a plurality of determinations of the local (site-specific) redox state of a liquid system, by employing a photoresponsive element, which can be independently irradiated at different sites to provide independently detectable signals.

35 Claims, 8 Drawing Figures

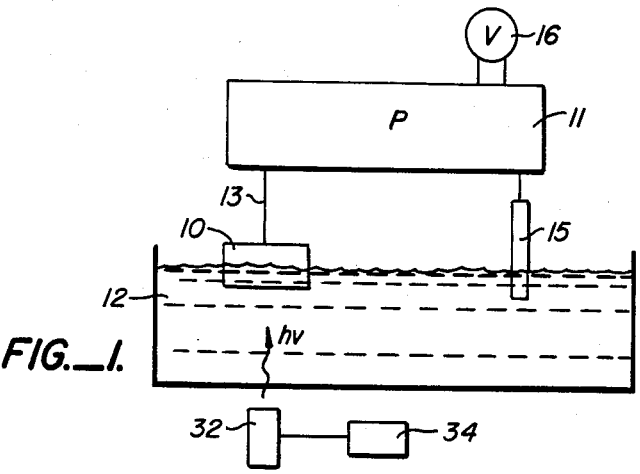
FIG._1.
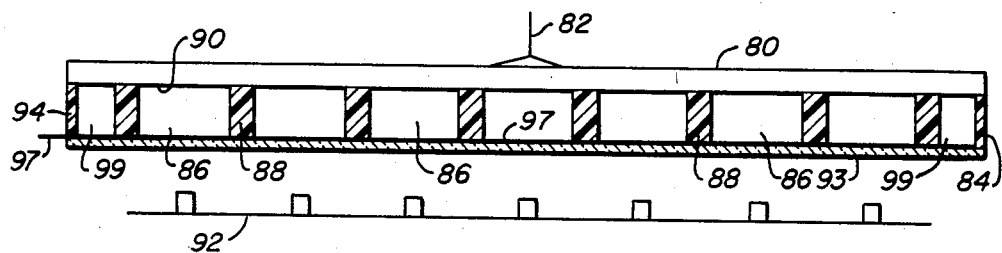
FIG._3.
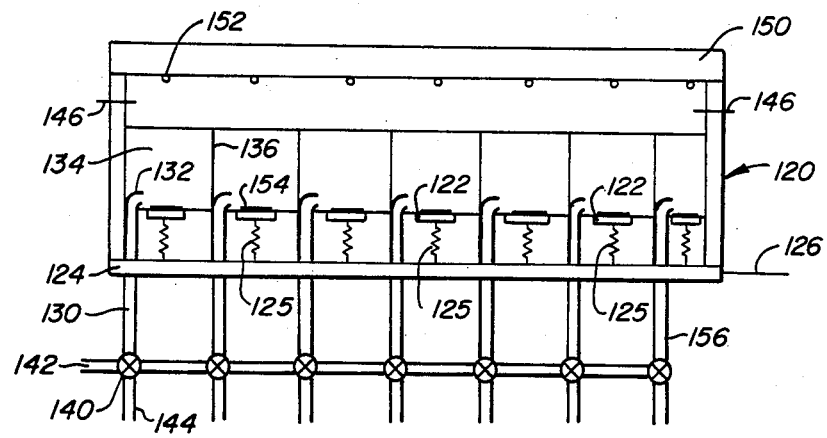
FIG._5.

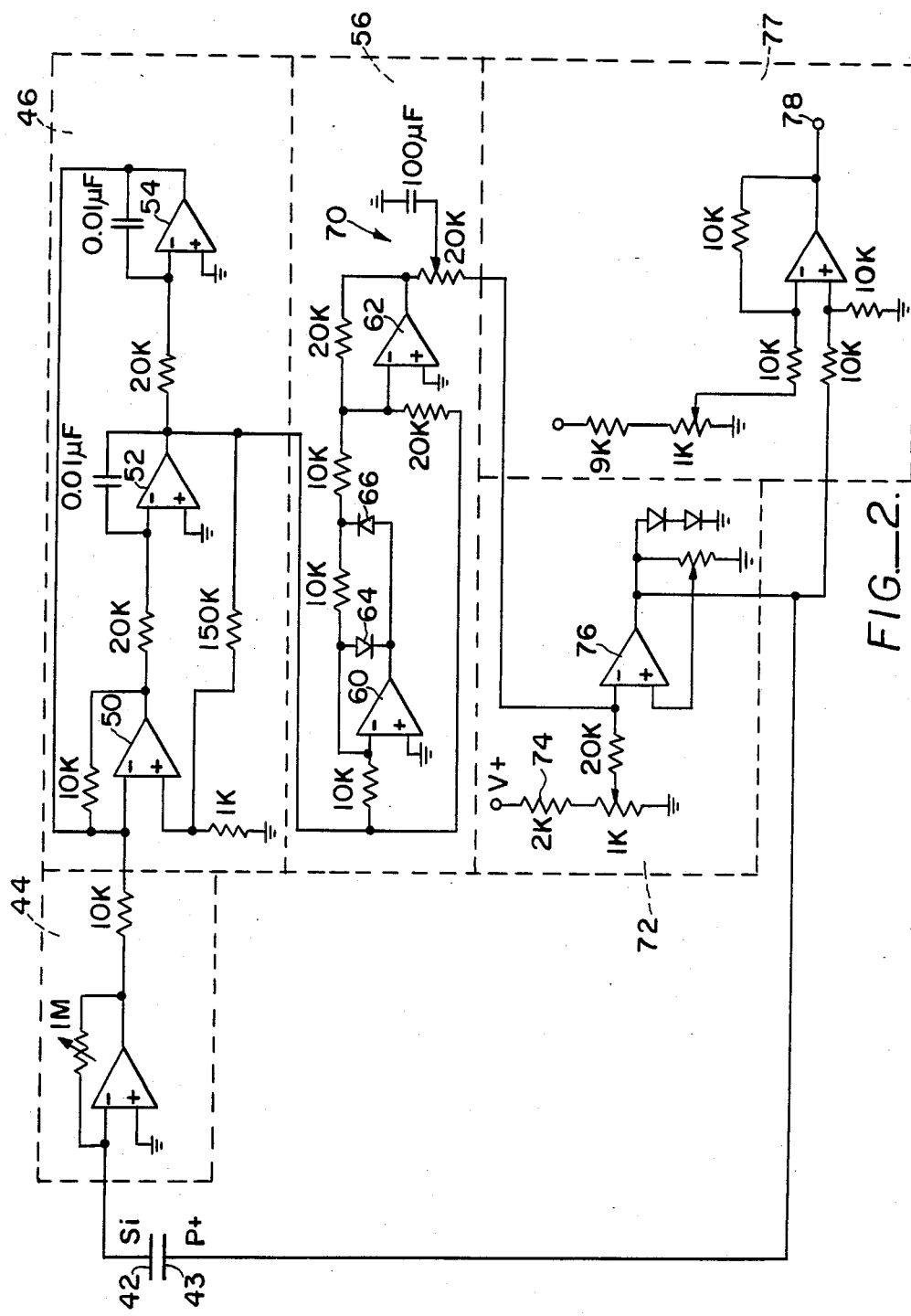
FIG._2.

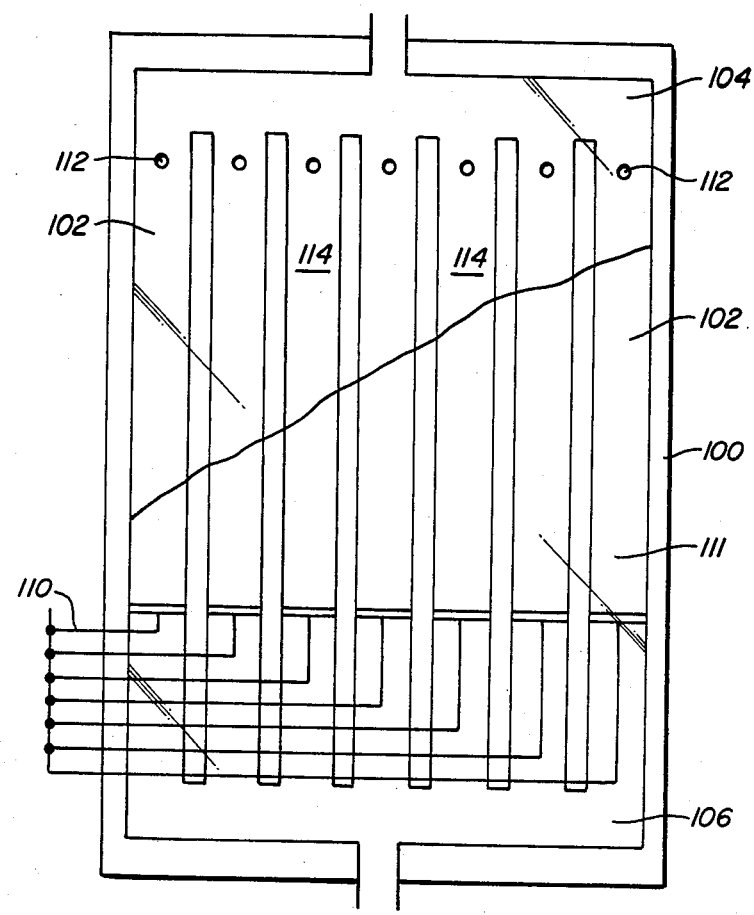
FIG._4.

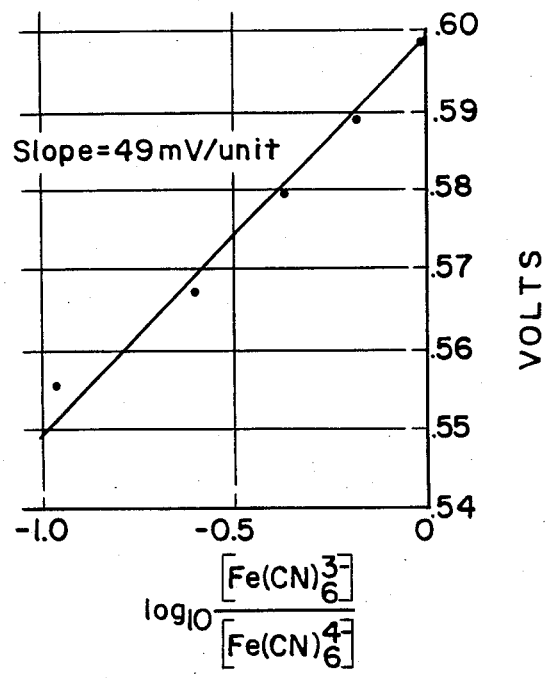
FIG._6.

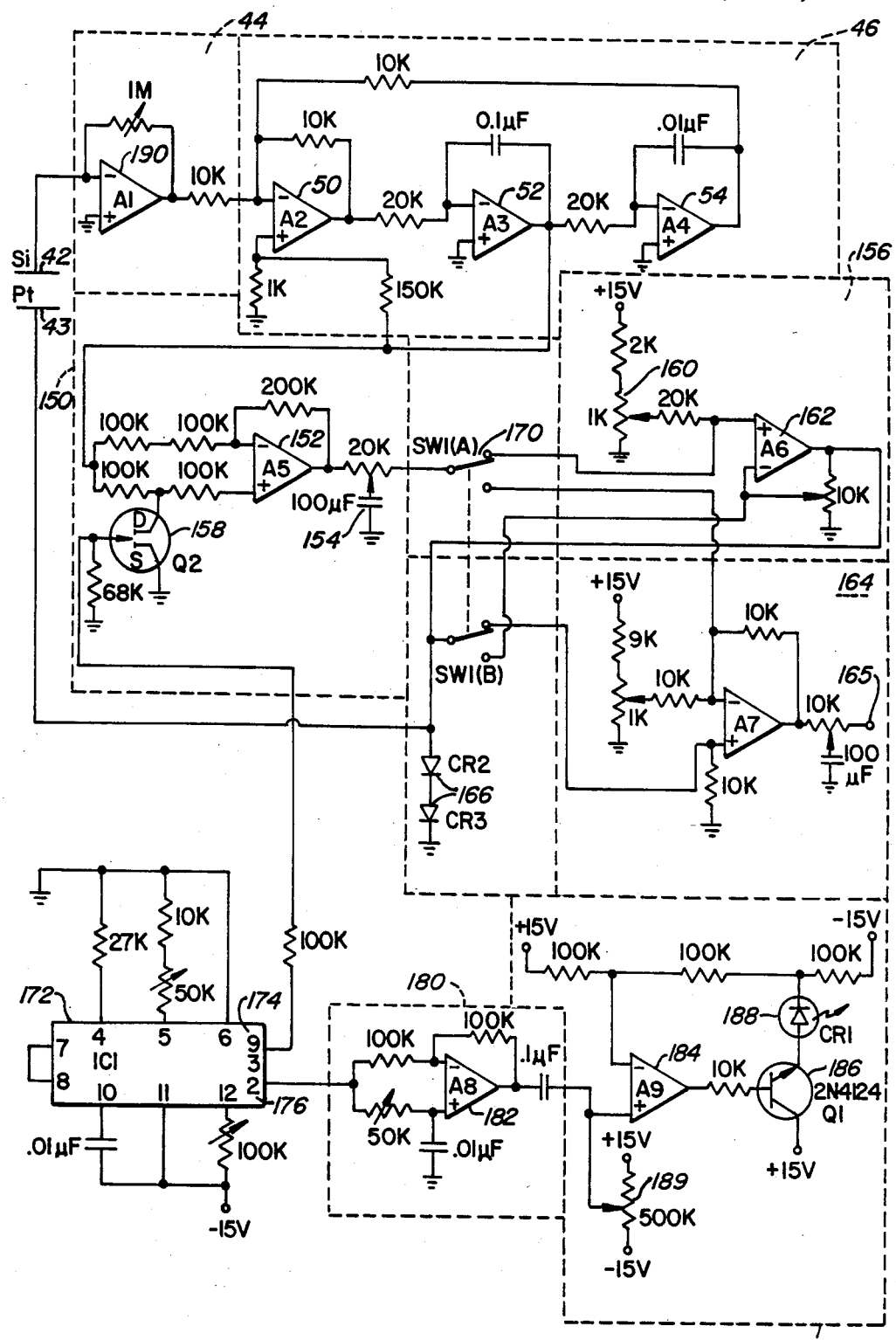
FIG._7.

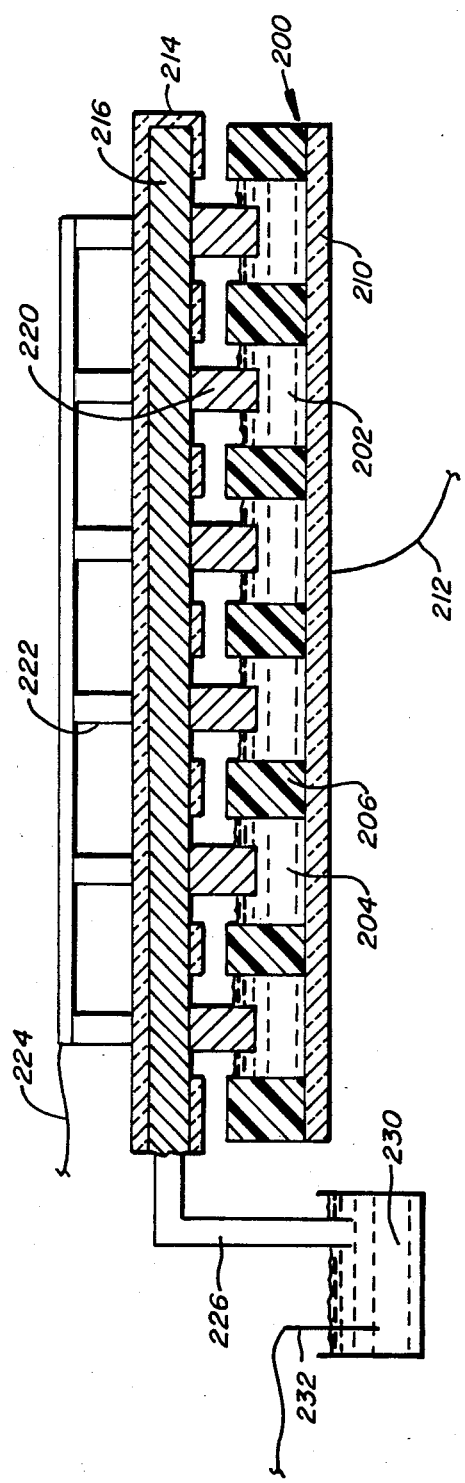
FIG._8.

PHOTORESPONSIVE REDOX DETECTION AND DISCRIMINATION

BACKGROUND OF THE INVENTION

1. Field of the Invention

The detection of the presence of a material and/or its amount in a particular environment becomes increasingly important in a society which seeks to monitor and manipulate its environment. Despite the long history of developing devices for measurement of various materials in liquid media, there still remain ample opportunities for improvements in sensitivity, efficiency, economy, and ease of use. Among the manifold detection methods, one device which has found recent application is the field effect transistor (FET) and various modifications of the device. Various studies have been directed to the use of FETs for measurement of organic molecules. See for example, Stenberg et al., *J. Coll. Interface and Sci.* (1979) 72:255-264; Bergveld and De-Rooij, *Med. Biol. Eng. Compt.* (1979) 17:647-654; Bergveld et al., *IEEE Trans. BMI*-23 (1976) pages 136-144; and Lauks and Zemel, *IEEE Trans. on Electron Devices*, Vol. ED-26, No. 12 (December 1979), pages 10959-10964. These references are merely illustrative of references directed to semiconductor devices, particularly field effect transistors, for measurement of materials in solution. The FET devices have not found commercial acceptance and in many situations, lack flexibility. For use as chemical detectors, FET devices particularly suffer from the difficulty of obtaining exposed gate regions and working with them in an experimental environment.

As compared to other devices, semiconductive or other devices which respond to an electrical signal provide for a number of advantages. The electrically responsive device can respond to relatively small signals. Furthermore, by various techniques, the signal can be modulated and the background noise diminished or substantially eliminated. Electrical devices can frequently be miniaturized, so that relatively small equipment can be developed for measurement of changes in various fluids.

2. Description of the Prior Art

References of interest include Gronet and Lewis, *Nature* (1982) 300:733-735; Bard and Faulkner, 1980. *Electrochemical Methods--Fundamentals and Applications*, John Wiley and Sons, New York; Fahrenbruch and Bube, 1983. *Fundamentals of Solar Cells--Photovoltaic Energy Conversion*, Academic Press, New York; Fonash, 1981; *Solar Cell Device Physics*, Academic Press, New York; and *Photoeffects at Semiconductor-Electrolyte Surfaces*, ed. Nozik, American Chemical Society, Washington, D.C., 1981. See also U.S. Pat. No. 4,293,310 and PCT Application No. WO83/02669.

SUMMARY OF THE INVENTION

Photoresponsive sensing elements, circuits and methods are provided involving measuring electrical signals resulting from irradiation at a plurality of sites, where the signals vary in relation to the redox environment at each site. A plurality of sites on a photoresponsive surface are irradiated with light of a predetermined wavelength range to produce individually analyzable signals, where each of the signals is related to the redox state of the medium volume associated with the irradiated site. The photoresponsive surface is polarized in relation to one or more counterelectrodes which is in an electrically transductive relationship through a medium with said photoresponsive surface.

BRIEF DESCRIPTION OF THE DRAWINGS

FIG. 1 is a first exemplary circuit for use in the method of the invention;

FIG. 2 is a second exemplary circuit which provides for the automatic maintenance of the photosignal from a photoresponsive surface at a predetermined value;

FIG. 3 is a diagrammatic cross-sectional view of a photoresponsive device for sampling multiple compartments;

FIG. 4 is a diagrammatic view partially broken away of a manifold for use with the photoresponsive device;

FIG. 5 is a diagrammatic view of a photoresponsive device and an associated sample handling system;

FIG. 6 is a graph of observed voltage with varying redox compositions;

FIG. 7 is a third exemplary circuit which allows for alternation between maintaining a constant potential or constant amplitude; and FIG. 8 is a diagrammatic cross-sectional view of an embodiment having a plurality of wells and a common gel electrolyte communicating with individual wells.

DESCRIPTION OF THE SPECIFIC EMBODIMENTS

In accordance with the subject invention, methods and devices are provided which allow for the simultaneous or substantially simultaneous determination of individual portions of a medium. The device employs a photosensitive sensing element serving as an electrode electrically coupled through a signal analyzing circuit and an electrically communicating medium to at least one counterelectrode. Sites on the photosensitive surface are individually irradiated by light of a predetermined wavelength range, whereby the signals at such individual sites may be individually analyzed. The detectable signal at each of said sites will be related to the level of irradiation at each site and the state of the conduction band within the photosensitive sensing element as a result of the fluid medium adjacent the site on the photoresponsive surface.

The photoresponsive electrode is polarized in relation to at least one counterelectrode. The two electrodes are in electrically communicating relationship, where the medium providing the communicating relationship may be the same as or different from the medium to be analyzed. A circuit is employed which provides for polarizing the photoresponsive electrode with either a reverse or forward bias, where current is either inhibited or allowed to flow through an electrically communicating non-metallic medium, usually a polar fluid medium, e.g., an aqueous medium. In some instances there will be a dark current, while in other instances a significant current will occur only during irradiation. In order to determine the state of an individual portion of a medium of interest, one irradiates a site in propinquity to said individual portion and measures the resulting signal as compared to a standard.

The photoresponsive electrode or sensing element or electrode can be a semiconductive material or photoconductive material. Semiconductive materials include such materials as silicon, gallium arsenide, gallium selenide, aluminum gallium arsenide, or the like. The semiconductive material will be either of the p- or n-type and, as appropriate, may employ such dopants as boron, aluminum, phosphorus, arsenic, antimony, or the like. The degree of doping may be varied widely, there being a wide variety of commercially-available doped wafers which can be used. The concentration of the dopant will normally vary empirically to provide the desired photoresponse, frequently being a matter of convenience, and will generally range from about $10^{10}$ to $10^{20}$ atoms/cc; usually for silicon the rating will be about 5-20 ohm-cm. Photoconductive materials include chlorogallium phthalocyanine. Rieke and Armstrong, *J. Am. Chem. Soc.* (1984) 106:47-50.

Various electrical circuits may be used to measure changes in photoresponsiveness of the sensing electrode which result from changes in the state of an individual portion of the medium. These electrical circuits may primarily measure changes in phototransductance which include photopotential, photoconductance, photocapacitance or photoinductance, or combinations thereof. The circuits will be chosen so as to provide maximal sensitivity for detecting small changes in the state of the medium. These measurements will be generally referred to as the photoresponse.

The observed signal from the circuit can be a result of a change in direct current, alternating current or the effect of a direct current on an alternating current.

The circuits employed allow for measuring different variables, such as AC amplitude, bias potential, DC amplitude, the AC component of the LED amplitude, the DC component of the LED amplitude, or the like. The variables can be interrelated automatically by varying the potential or light intensity in relationship to the photoresponse. For example, one can vary the bias potential to maintain a constant AC or DC photoresponse and measure the change in bias potential; or, one can fix the bias potential and measure the DC current resulting from steady illumination or AC current resulting from amplitude modulated illumination; or, one can fix the amplitude of the AC or DC photoresponse by varying the intensity of the AC or DC illumination and measuring the light intensity.

Where wafers are used, they may come in a variety of sizes and shapes, varying from chip size which may have its largest dimension of about 0.1 mm or wafer size, which may be 100 mm, more usually not more than about 75 mm in its largest dimension. The device will usually have at least one smooth surface or smooth portion of a surface, desirably flat, which will serve as the irradiation site. The wafer may be round, rectangular, elongate or the like. The thickness of the wafer will generally be not more than about 1mm, usually less than about 2 mm, and generally not less than about $0.05\mu$, usually not less than 0.1 mm.

The irradiation surface will normally have an associated matrix. The matrix may include a coating of at least about 25 Å, more usually at least about 50 Å, which may be substantially larger, depending upon its function, usually not exceeding 1000 Å, more usually not exceeding 500 Å. For the most part, the matrix will include at least a small amount of a protective oxide or nitride coating or other protective coating, e.g., silicon oxide or nitride.

Alternatively or in combination, the surface may be reacted with a wide variety of organic silanes, particularly halides or esters, which can provide for an organic coating of the surface. The organosilanes will have organogroups of from 1 to 30, more usually of from about 1 to 25 carbon atoms, which may be aliphatic, alicyclic, aromatic or heterocyclic, or combinations thereof, usually hydrocarbon, which may be aliphatically saturated or unsaturated or may be a substituted hydrocarbon having a polar terminus, which may be polar due to: (1) a charge, e.g., carboxylate, phosphate or ammonium; (2) a zwitterion, e.g., betaine; or (3) a dipole, e.g., 3,4-dinitrophenyl, carboxylate ester, phosphate triester, etc.

Where hydrocarbon groups are employed, particularly aliphatic groups of from about 6 to 24 carbon atoms, either saturated or unsaturated, a second layer may be employed to provide for a bilayer membrane. Any lipids may be used for preparing the second layer which provide a stable bilamellar membrane. Alternatively lipids forming stable lamellar membranes may be employed for both layers, avoiding covalent bonding to the surface. Illustrative groups include phospholipids, sphingomyelins, gangliosides, cholesteric compounds, acylglycerols, waxes, and the like.

Conveniently a polymerized lipid bilayer may be employed which may be preprepared and positioned on the surface. See, for example, Wegner, Chapter V, R. A. Welch Foundation Conf. on Chemical Research XXVI Synthetic Polymers, Nov. 15-17, 1982, Houston, Tex., which disclosure is incorporated herein by reference. Desirably, the degree of polymerization will be less than 100%, usually from about 20% to 90%, to allow for a substantial degree of fluidity and lateral diffusion. If desired, a first layer may also be employed under the polymerized layer.

Various other materials may be used in conjunction with the surface, which materials may be bound either covalently or non-covalently, or held mechanically in place adjacent to the surface. The materials may be naturally occurring, or synthetic or combinations thereof. These materials include porous films, generally of from about 1 to 50 mil in thickness, normally being polar materials, such as nitrocellulose, partially hydrolyzed polyvinyl acetate, polyacrylates, proteins, polysaccharides, e.g., agarose, etc. Various gels may be used, such as agar, polyacrylamide, or the like. These layers may have independent integrity or rely on the photoresponsive device for support. They will be in contact, in whole or in part, with the photoresponsive element, either directly or through intermediate layers, e.g., liquid layers, such as aqueous layers.

Of particular interest are redox materials which may be bound covalently or non-covalently to the photoresponsive surface or a confronting surface. Various compounds which can act as election transfer agents may be employed using convenient linking groups, such as alkylenesilyl halides or esters. See, for example, Faulkner, *Chemical and Engineering News,* Feb. 27, 1984, pp. 28-45, where N,N'-disubstituted 4,4'-dipyridyl compounds are described. Other silylhalide substituted redox compounds may be employed, which will be described subsequently.

Various other materials may also be associated with the photoresponsive electrode, which materials will be described in more detail subsequently. Among these may be a confronting spaced apart layer, e.g, sheet or slide. Other materials may be present to provide for specific interactions, particularly complexation between specific binding materials. These materials may be bound directly or indirectly to the photoresponsive surface, or to the protective coating, or confronting layer.

Any films or coatings or layers should not interfere with the transmission of light of the particular wavelength with which the photoresponsive surface is irradiated. Furthermore, a matrix at the photoresponsive surface may be required to allow for polar interactions as a result of ions or the binding or complexing of polar, particularly charged materials, e.g., proteins, lipids, neuraminic acids, or other charged saccharide, or the like.

The matrix may be of any thickness, so long as it allows for sufficient transmission of light to the semiconductor surface for the desired intensity and for the particular modification of the state of the medium at a site at the surface. The medium employed at the site of the surface will usually allow for diffusion of ions. Therefore, to the extent that solid films are employed, these will usually be porous and immersed in a liquid medium, so as to allow for the diffusion of ions and molecules adjacent the sensing electrode surface to provide for electrical communication between the electrodes.

The device may have a single continuous photoresponsive surface ranging from a surface area of about 1 mm$^2$ to about 50 cm$^2$, more usually about 25 cm$^2$, or in some instances may be a plurality of individual photoresponsive surfaces physically isolated from each other, but electrically connected to the same circuit. The individual units will usually range from about 0.1 mm$^2$ to 5 mm$^2$ or greater, the upper limit being primarily one of convenience, although in some situations an enhanced signal may be obtained by employing a large surface area. The individual units may be in contact with media which are completely isolated or are partially isolated from each other by the presence of partitions which allow for electrical communication, for example, membranes, fritted walls or partitions extending only a partial distance to the surface, conveniently 25% to 90% of the distance to the surface. Such partitions may also find use with a large photoresponsive surface, as will be described subsequently.

Access for media to different regions of the photoresponsive surface may be controlled physically in a variety of ways, providing for compartments, which may have any convenient periphery, circular, square or the like, channels, which may be circular, serpentine or straight, or combinations thereof. Extended areas such as channels allow for inspection of a moving solution at different times. Channels can be provided by having grooves in the matrix associated with the photoresponsive surface and compartments can be provided for by having identations in the matrix associated with the photoresponsive surface. The number of independent units to be measured may be 2 or more, usually being 5 or more, and may be 50 or more, and could be as high as 2500.

Alternatively, a facing solid film, layer or plate may be employed, which may provide for localization of key reagents or for appropriate structure, resulting in dividing the photoresponsive surface into compartments and/or channels. The facing surface is normally rigid and may be transparent, opaque, translucent, may be metal, ceramic, glass, or the like. Where translucent or opaque, in relation to the irradiation light, where the facing plate is adjacent to the photoresponsive surface, holes can be provided in the plate for transmission of the light at a variety of sites. Or, optical fibers may be employed for directing light through the plate to particular sites. The plate may be an inert material, merely providing structure, or can be modified by providing for binding of various materials to the surface. These materials would be involved in the determination of the state of an incremental portion of a medium, so as to provide for individual sites which may be individually determined, allowing for the rapid determination of a plurality of results.

Irradiation of the photoresponsive surface may be on either side of the wafer. However, where the irradiation occurs on the side opposite to the side associated with the medium of interest, it will be necessary that the wafer be very thin, so that the conductive band which is influenced by the medium of interest can also be affected by the light irradiation. Normally, in this situation, the thickness of the photoresponsive element will be from about 0.05$\mu$ to 2$\mu$.

The light source can be any convenient source, particularly of an energy at least about the conduction band gap of the photoresponsive element, so as to produce mobile charges, i.e., free electrons and positive holes. The light source will generally vary in the range of visible to infra-red; for silicon, this is about 1.1 eV. This would provide for a wavelength range generally in the range of about 0.1$\mu$ to 1$\mu$, more usually from about 0.3$\mu$ to 1$\mu$. Other semiconductors can be matched with a light source accordingly. By employing dyes as a thin layer on the photoresponsive surface, lower energy light may be employed coupled with a rednx reaction. The light and dark periods for pulsed radiation may be the same or different, generally ranging from $10^{-2}$ to $10^{-6}$ seconds. The total time of irradiation of a particular site is not critical and may range from $10^{-3}$ to 100 seconds.

Any source of light may be used which provides the means for providing continuous or intermittent light for short periods of time, particularly a source which can provide for cycling the light at a predetermined frequency, e.g., 100 Hz–100 kHz, usually 100 Hz–50 kHz, more usually 1–20 kHz, during the period of irradiation. Of particular interest are LED arrays, which are available providing red light, or white light, for example, from a tungsten lamp. Alternatively, a single source can be used, e.g., fluorescent light in the visible region; where shutters are used, nematic liquid crystals, gratings, optical fibers, choppers, or the like, may also find application.

Usually, the different sites will be irradiated at different times to provide a simple method for distinguishing between the signals associated with the individual sites. However, simultaneous irradiation of different sites may be employed, where a means is used to allow for distinguishing the signals, such as a phase shift, alternating frequencies, or other combinations where the signals can be segregated.

As indicated above, the subject application can address one or more individual portions of one or more media to be analyzed, where the individual portion or volume can be indicative of the gross properties of the medium or particular individual portions of the medium, where properties of individual portions may differ in their properties one from the other as well as from the properties of the gross medium. One can inspect individual portions by irradiating a site on the photoresponsive surface associated with the particular individual portion. Irradiation at a particular site may be achieved by employing a light source which irradiates the specific site, due to movement of the light source and the photoresponsive surface in relation to one another or by having a plurality of light sources, which irradiate different portions of the photoresponsive surface in accordance with a predetermined schedule, or combinations thereof. In this way, one can address different portions of the medium to determine the state of the individual portion as to a variety of properties and determine variations in the state of the medium over a large volume. Furthermore, one can employ one or more channels and determine the state of the individual portions along a channel, so that one can relate variations in the states of the individual portions along the channel to a temporal change occurring in the medium. By using continuous or intermittent flow techniques, by mixing two media which provide for a detectable reaction prior to entering the irradiation path, one can provide a steady state at each irradiation site along the channel. In this manner, one can determine rates of reaction, by observing the steady state properties of the medium at different sites along a channel.

Thus, the subject invention allows for the substantially simultaneous monitoring of temporal events. Therefore, one can choose to move either one or more light sources or the photoresponsive surface or have a plurality of light sources, which will irradiate a surface in accordance with a predetermined schedule, or, with a plurality of isolated photoresponsive, surfaces have simultaneous irradiation or irradiation at differing times.

Because of the diversity of redox materials which can be detected, the permissible variations in the conformations which can be employed, and the flexibility in circuitry, a wide variety of different systems and situations can be addressed by the subject invention. While for the most part, fluids providing for modulation of a photoresponsive electrical signal will be monitored, the subject invention allows for monitoring of solid and semi-solids in appropriate situations.

The subject invention can be used for monitoring various streams, such as effluents, natural bodies of water, industrial streams from chemical processing plants, refineries, power generation, and the like, air, or other fluid, where the fluid has a component which will affect a photoresponsive electrical signal or such component can be employed in conjunction with other materials to provide for such a response.

A photoresponsive electrode can be influenced by the redox potential of the medium adjacent the wafer surface. Various redox systems can be employed which can be in vitro or in vivo systems involving cells, e.g., microorganisms, mammalian cells, etc., enzyme reactions, particularly oxidoreductases, e.g., glucose oxidase, peroxidase, uricase, NAD or NADP dependent dehydrogenases, naturally occurring electron transfer agents, e.g., ferridoxin, ferritin, cytochrome C, and cytochrome $b_2$, organic electron donors and acceptor agents, e.g., methylene blue, nitro tetrazolium, Meldola blue, phenazine methosulfate, metallocenes, e.g., ferrocenium, naphthoquinone, N,N'-dimethyl 4,4'dipyridyl, etc., and inorganic redox agents, e.g., ferri- and ferrocyanide, chloronium ion, cuprous and cupric ammonium halide, etc.

In another embodiment, one could monitor the change in biological oxygen demand or chemical oxygen demand of an effluent stream or river by having a plurality of channels, which can divide up the stream into numerous individual channels, where different chemicals could be introduced into each individual channel, where the chemical or the product of the reaction provides for modulation of the photoresponsive electrical signal. Where there is a change in the redox potential, the rate of change can be determined by determining the change in electrical signal at different sites along the channel and relating the rate to the chemical or biological oxygen demand.

One can use the subject device for measuring rates of reactions, such as enzymatic reactions, where the enzymatic reaction results in a change in redox potential of the medium. This can be done in a dynamic or static way in that by employing a moving stream, one can make the rate determination substantially instantaneously. Alternatively, by having a relatively static solution at a particular site, which is irradiated intermittently, and readings taken at different times, one can also determine the rate. The device may be used to determine the enzyme-catalyzed rate of reaction, where the enzyme catalyzes reduction of excess substrate using electrons generated at the wafer surface. In such cases, rate of reduction (and hence concentration of enzyme) determines the DC current flow at the surface of the wafer (and hence the change in the measured photoresponse). In such cases (e.g., as for horseradish peroxidase) enzyme concentration may be measured over a period as short as 1 to 5 seconds.

The subject invention can also be used with semi-solid or solid media, employing appropriate adaptations. For example, chromatographic layers, gels or the like, can be used where a redox signal is associated with a component of interest, where a mixture has been separated into components by thin layer chromatography, electrophoresis, density gradients, etc.

Of particular interest will be the use of the subject invention in detecting the presence of a specific component of a medium, where the component may be a chemical, either synthetic or naturally occurring, such as drugs, hormones, proteins, steroids, receptors, nucleic acids, or the like; or aggregations of chemicals, such as nucleosomes, viruses, cells, both prokaryotic and eukaryotic, or the like. These determinations will frequently be made in physiological fluids, such as blood, plasma, saliva, cerebrospinal fluid, lymph, urine, or the like.

In some cases, such determinations will involve a combination of a ligand and receptor, where the ligand and receptor have a specific affinity, one for the other, so that they provide a pair of specific binding members. Receptors for the most part will be antibodies, enzymes, or naturally occurring receptors, and can for the purposes of this invention include nucleic acids, while ligands may be any compound for which a receptor is available or can be made.

One could analyze for DNA or RNA sequences, e.g., alleles, mutants, recombinants, etc., by having labeled oligonucleotide sequences which provide for a redox reaction. For example, one could bind probes to a glass surface, with different oligonucleotide sequences at different sites. The DNA or RNA sample would be prepared by denaturing any double-stranded polynucleotide, e.g., ds DNA, and mechanically, e.g., by shearing, or enzymatically, e.g., one or more endonucleases, providing an average-sized fragment, ranging from 500 to 10,000 nt.

The sample would then be mixed with labeled sequences which homoduplex with the bound oligonucleotide sequences, so that the labeled sequences compete with the sample sequences for the bound sequences under hybridization conditions of a predetermined stringency. After sufficient time for the homologous sequences to become bound to the glass surface through the intermediacy of hybridization to the bound sequence, the slide is removed, washed and placed in juxtaposition to the photoresponsive surface, where a solution between the two surfaces provides for a redox reaction with the label.

The systems involving specific binding pairs may be varied widely and may involve a "homogeneous" system, where there is no binding to a solid surface or a "heterogeneous" system, where there may be binding, which binding is renewable or non-renewable. By "renewable" is intended that one can remove an active component of the assay system from the surface and replace it with a different component.

For the most part, an aqueous buffered medium will be employed, which may be lightly or heavily buffered depending on the nature of the material generating the signal. Various buffers may be employed, such as carbonate, phosphate, borate, tris, acetate, barbital, Hepes, or the like, at concentrations in the range of about 0.01 to 0.5M. Organic polar solvents, e.g., oxygenated neutral solvents, may be present in amounts ranging from about 0 to 40 volume percent, such as methanol, ethanol, α-propanol, acetone, diethylether, etc.

In the specific binding pair assays, there will be a label conjugated to a substance, where the modulation of the photoresponsive signal will be related to the amount of analyte in the sample being assayed. The substance may be the analyte, analyte analog, the complementary binding member or a substance binding to any of these substances. Such substances include antibodies to the immunoglobulin of a species, e.g., sheep antibody to murine immunoglobulin. Also included are pairs, particularly hapten-receptor pairs, where the substance is modified with a hapten, e.g., biotin, and a reciprocal binding member labeled, e.g., avidin. Thus, the label may be bound directly or indirectly, covalently or non-covalently, to a member of the specific binding pair which includes the analyte.

A system is employed which may have one or more components which provides a redox material in relation to a photoresponsive site which modulates, directly or indirectly, the photoresponsive electrical signal. A substantial diversity of modulating materials may be employed in the specific binding assays, which materials may be the result of a catalyzed reaction, e.g., an enzyme catalyzed reaction.

For the homogeneous system, it will only be necessary that binding result in modulation of an assay system which results in the redox modulation of the photoresponsive electrical signal. The binding can occur adjacent to the photoresponsive surface or distant from the photoresponsive surface, where the photoresponsive surface can be used later to determine the level of the detectable compound in the assay medium. For example, one could carry out a plurality of assays in separate containers, e.g., microtiter plate wells, where the redox potential of the medium is changed in each of the wells in accordance with the amount of an analyte. One could then simultaneously or serially transfer aliquots of each of the sample media to individual compartments having the photoresponsive surface as the bottom of each of the compartments. The individual samples would then be screened by illuminating each compartment in turn and determining the signal associated with the irradiated sample medium. Alternatively, the monitoring of the assay reactions could be carried out with the photoresponsive surface at the bottom of a plurality of compartments as depicted in FIG. 8. Or, the assay can be carried out adjacent the photoresponsive surface, by having a number of partial partitions extending only a portion of the distance through the assay medium and introducing the sample adjacent the photoresponsive surface. Since the rate of formation of the detectable product will vary with the amount of analyte in the compartment, by comparison of differences between compartments having known amounts of analyte and compartments containing the sample, one can relate the result to the standards.

Homogeneous assays include such assays as described in U.S. Pat. Nos. (label) 3,817,837 (enzyme); 3,935,074 (any ligand); 4,160,645 (non-enzymatic catalyst); 4,193,983 (liposome); 4,208,479 (enzyme modifier); 4,275,149 (particles); and 4,341,865 (suicide inhibitors), which appropriate parts are incorporated herein by reference. These patents involve enzymes, redox reagents, and combinations thereof.

For example, there is a commercial assay sold under the trademark EMIT. The assay employs the enzyme glucose-6-phosphate dehydrogenase, which produces NADH from NAD. By providing for an oxidation at the photoresponsive surface, which converts the NADH to NAD, either directly or through the intermediacy of other redox compounds, the rate of formation of NADH by the enzyme may be determined.

The homogeneous enzyme assay employs antibodies to an analyte, where the analyte or an analyte analog is also bound to the enzyme to provide an enzyme-analyte conjugate. When antibody to the analyte binds to the enzyme-analyte conjugate, the enzymatic activity is substantially reduced. Thus, the rate of formation of NADH can be determined and related to the amount of analyte present in the volume adjacent the photoresponsive site.

In carrying out the assay, one could have the photoresponsive site with a plurality of partitions defining a plurality of compartments, where the assay medium extends beyond the partitions. The assay medium would include the enzyme conjugate and buffers, stabilizers, or other additives, which are not directly involved in the system providing for the detectable signal. One would prepare a sample solution containing the antibody, the sample, and appropriate substrates, the mixture incubated, and then injected into the appropriate compartment. The rate of production of a redox reagent, could then be followed as indicative of the amount of analyte present in the sample.

Besides having an enzyme conjugated to the analyte or reciprocal binding pair member, one can also conjugate substrates, co-factors, suicide inhibitors, or the like. Various of these techniques are disclosed in U.S. Patents described above. Therefore, one could prepare a conjugate comprising a suicide inhibitor and an analyte. One could bind enzyme, either covalently or non-covalently, to a surface, either the photoresponsive surface or a surface adjacent to the photoresponsive surface. A sample solution would be prepared of antibody to the analyte, the sample, the suicide inhibitor conjugate, substrates, and any additional reagents necessary for producing a detectable product. One could then add the sample solution to the enzyme bound to the surface and determine the enzyme activity.

The heterogeneous system allows for separation between complexes between specific binding pairs and uncomplexed specific binding pair members. This is achieved by having one of the members of the specific binding pair bound to a solid surface. One could prepare a clear slide having specific antibodies at different sites on the slide, so that one could assay a sample for a plurality of analytes. One would then add antibodies for each of the analytes to the solution, so as to employ a sandwich immunoassay. Conveniently, the antibodies would be monoclonal antibodies to minimize cross-reactivity. One would then add an enzyme conjugate to an antibody which is specific for immunoglobulins from a particular species. For example, if the monoclonal antibodies are murine, one could conjugate rabbit antibodies specific for murine immunoglobulin with a suitable enzyme which provides for a redox reaction, e.g., peroxidase. Thus, only where the monoclonal murine antibody had bound, would there also be enzyme conjugate. One would then place the clear slide adjacent the photoresponsive surface in registry, so as to define where each of the original antibodies were. A thin, liquid film at the surface would provide the appropriate reagents and substrates for reaction with the enzyme to produce the detectable event. One would then irradiate the surface sequentially through the clear slide to determine whether any enzyme had become bound at a particular site. In this manner, a sample could be assayed for a large number of different analytes, substantially simultaneously to provide for a complete battery of determinations on a single sample, where extremely small amounts of the sample would be required.

Heterogeneous techniques are described in U.S. Pat. Nos. 3,654,090 (enzyme); 3,791,932 (enzyme); and 4,134,792 (enzyme substrate), which patents are in appropriate part incorporated herein by reference.

If one wished to repeatedly use the same surface, one could apply a member of a specific binding pair to the surface, where the complementary member is conjugated to a member of a specific binding pair related to the analyte. For example, one could coat the surface with the same or different sugars, haptens, receptors, antibodies, or members of naturally occurring ligand-receptor pairs. One would then conjugate the member of the specific binding pair related to the analyte to the binding member complementary to the material bound to the surface. To illustrate, one could coat the surface with a saccharide and conjugate the analyte related specific binding pair member, e.g., antigen, to a lectin. Thus, one could prepare conjugates of antibodies to a protein analyte and lectins. By adding a solution of the antibody-lectin conjugate to the saccharide-coated surface, the antibodies would become bound to the surface. One could then carry out the assay as described above and after completing the assay, remove the complexed material from the surface by adding a concentrated solution of the saccharide. One can use other pairs by analogy, where in place of a lectin, an antibody or natural receptor could be employed. Thus, a single surface can be used which could be repetitively replenished, so that the same or different types of assays may be employed after each determination. By binding different compounds to the surface at different sites, one can direct specific binding pair members to a specific site with the appropriate conjugate.

Various techniques may be used with enzymes for amplification and enhanced sensitivity. One may employ enzymes which require co-enzymes or substrates which can be produced by another enzyme, the interaction between the enzymes referred to as "channeling." For example, one could bind a first enzyme to the slide and have the second enzyme conjugated to the receptor. Thus, the first enzyme could provide for a high localized concentration of the substrate or co-enzyme for the second enzyme. Illustrative enzyme pairs include glucose oxidase and horseradish peroxidase, which can act to oxidize an electron transfer compound, a kinase and G6PDH, which with glucose and NAD can produce NADH, which can then be coupled with an electron transfer agent, etc. The rate of formation or instantaneous concentration of the electron transfer agent could be related to the presence of an analyte.

Catalysts other than enzyme catalysts may be used, particularly redox catalysts. These catalysts may include such compounds as phenazine methosulfate, methylene blue, nicotinamide adenine dinucleotide, Meldola blue, flavin mononucleotide, ferri- and ferrocyanide, and the like. These compounds may be used in conjunction with enzymes or other catalytic compounds to provide for a redox potential or current flow at the photoresponsive surface. For example, instead of conjugating receptors with enzymes, one could conjugate receptors with phenazine methosulfate, Meldola blue, methylene blue, etc. By then employing the couple of NADH and an electron transfer agent, a modified signal would be produced at the photoresponsive sensing electrode.

Redox reagents can be coupled with naturally occurring enzyme transport systems involving cells, membrane fragments, or individual members may be joined in vitro or the individual members may be independently dispersed in the medium. Thus, amplification can be achieved. Alternatively, the presence of intact cells or cell fragments can be detected by their influence on a redox couple. For example, methylene blue may be added to a medium suspected of containing microorganisms, e.g., bacteria, which are chemically reductive. Prior reduction of the methylene blue can be rapidly detected as indicating the presence of reductive microorganisms.

In many situations it will be of interest to determine the presence of a natural receptor in a physiological fluid, particularly blood or plasma. Usually, the receptor will be an antibody, resulting from an autoimmune disease, foreign substance, or an infection. The antibody may be detected in a competition assay, where the endogenous antibody competes with labeled antibody for the complementary antigen or the antibody may serve as a bridge to bind labeled antigen to antigen bound to a surface or particle. Otherwise, for the most part, the antibody assay would follow the techniques employed for detecting antigens.

In some situations it may be desirable to have lipid mono- or bilayers covalently or non-covalently bound to the photoresponsive surface or other surface which can be brought in proximity to the photoresponsive surface. A single lipid layer may be formed by first employing aliphatic silyl halides or esters, where the silyl compound may have from one to three aliphatic chains, generally of from about 12 to 24 carbon atoms, more usually of from about 12 to 20 carbon atoms. In addition, other materials may be present, either bonded to a silyl group or bonded to the aliphatic chain, including aryl groups, functionalities, e.g., carboxyl groups, halo groups, amino groups, or the like. One can then provide for the second layer by dipping the surface through a lipid monolayer.

A lipid bilayer may also be formed without covalent bonding to a hydrophilic surface of a wafer by first passing a silicon wafer in a perpendicular orientation (normal to a lipid monolayer on an aqueous surface in a Langmuir trough, for example) down through a lipid monolayer at the air-water interface into the water layer and then raising the wafer back through the interface parallel to the monolayer. The bilayer is then formed by returning the wafer through the interface face down and parallel to the interface. A thin aqueous film can be maintained between the wafer surface and bilayer.

The bilayers allow for lateral diffusion within the layer. One can provide for various groups bound to lipids which will specifically bind to an analyte, e.g., antibodies. One could provide for the presence of different enzymes bound to different antibodies, each antibody being specific for different antigens on a cell surface, where the enzymes are related by the product of one being the substrate of the other. The enzymes would thus provide for channeling. The presence of the cell will bring together the related enzymes resulting in an enhanced rate of production or destruction of an electron transfer agent capable of modulating a signal from the sensing electrode.

The use of bilayers can also be coupled with ionophores as labels, where the ionophores allow for transport of ions through the bilayer to the photoresponsive surface. Thus, ionophores may be coupled to specific binding partners, e.g., ligands or receptors which would specifically bind to their complementary partner bound to the bilayer. The presence of the free ionophore would modulate the photoresponse due to the enhanced concentration of ions in close proximity to the surface. Illustrative ionophores include mellitin, nonactin, valinomycin, alamethicin, crown ethers, and the like.

One of the advantages of the subject invention is that it may use chemistries developed for use with spectrophotometric or fluorometric detection systems. For example, biotin modified nucleic acids are described for use as probes. By coupling an appropriate enzyme to avidin, one could probe a DNA or RNA sample fixed to a surface with the biotin modified probe under stringent hybridization conditions. After removal of non-specifically bound probe, one would add the avidin enzyme conjugate and additional members of the redox system.

For example, the enzyme 1,6-bisphosphate aldolase may be employed as the label, and fructose-1,6-diphosphate and ferricyanide provided. Depending on the nature of the photoresponsive surface, one could detect the change in the $Fe^{+3}/Fe^{+2}$ ratio.

Alternatively, a coenzyme could be used as a label such as FMN, FAD or NAD which could be coupled with an enzyme and a second redox couple, where the rate of transformation of the second redox couple would be related to the amount of coenzyme present.

Alternatively, a sample containing a plurality of microorganisms may be spread on an appropriate nutrient agar gel and cloned. Employing the Grunstein-Hogness technique, cells are transferred to a nitrocellulose porous film in appropriate registry with their position on the gel, lysed and the DNA fixed to the film by heating. Probes having a complementary sequence to a unique sequence of the organism of interest are provided as partial single strands with a double-stranded 3'-terminus having a sequence specifically recognized by a protein, e.g., repressor, rho, N protein of lambda, or the like. The film is contacted with the probe under hybridizing conditions, e.g., 50% aqueous saline dimethyl formamide and the hybridization solution then removed. After washing the film, a solution is added containing a specific binding receptor labeled with an enzyme which catalyzes a reaction which modifies the redox potential of the medium. After sufficient time for the labeled protein to bind, the film is washed free of non-specifically bound protein and placed in close-facing juxtaposition to the photoresponsive surface. The enzyme substrate is then added and the signal from the sensing electrode determined.

The microorganisms can also be used to measure the presence of a biostat or biocide in a medium. By combining the medium with growing microorganisms and determining the rate of growth of the microorganisms as compared to a standard differing only in the absence of the medium the presence of a biocide can be detected. By employing immortalized mammalian cells, e.g., tumor cells, the presence of growth regulators can also be detected.

The following examples are illustrative of the manner in which the subject methodology could be used. The device, either a single surface or a plurality of individual non-contiguous surface units, has partitions to isolate individual areas or compartments. A film is employed proximate to the surface having lectins specific for a particular mono- or oligosaccharide. Antibodies are modified with the particular saccharide and antibodies for the same or different ligands are introduced into each compartment and the excess washed away. A sample is now introduced which overflows the compartment partitions and any complementary ligand becomes bound in the appropriate compartment. The sample is then washed away and an antibody mixture added which binds to the single or multiple ligands bound to the antibodies in the compartments. These antibodies are all from a single source, e.g., mice. The antibody solution is washed, a conjugate of an enzyme with rabbit antibody to mouse immunoglobulin is added and allowed to overflow the compartment walls and bind to any mouse immunoglobulin in the compartments. The non-specifically bound enzyme may then be washed away and the enzyme activity in each compartment determined by adding a substrate medium to each compartment which provides a product which can be photoresponsively determined.

In another embodiment, individual photoconductive units are provided having antibodies covalently bonded to the surface of each unit through a silyl-substituted aliphatic carboxylic acid. The sample is then contacted with the antibody, the sample washed away and enzyme-conjugated-antibody added. After sufficient time for binding, non-specifically bound enzyme is removed and a developer solution added which produces NADH. Under suitable conditions NADH produced by the enzyme can be indirectly reoxidized by the photoresponsive electrode so that the NAD may be recycled. The rate of formation of NADH is related to the photoresponse as a result of photooxidation.

Various circuits may be employed for determining the state of the medium adjacent the surface. Besides the photoresponsive sensing electrode, there will be at least one counterelectrode, preferably two counterelectrodes, and there may be a counterelectrode for each compartment or channel of the device. The same or different electrode may serve as a controlling or reference electrode.

Various electrodes of a variety of materials may be used, so long as the materials of the electrode do not adversely affect the photoresponsive electrode, are not adversely affected by, and preferably not sensitive to the electrically communicating medium, and do not adversely affect the electrically communicating medium. Illustrative electrodes include such materials as platinum, rhodium, palladium, silver-silver chloride, calomel, conducting glass electrode ($SnO_2$, $InO_2$ or ITO), etc. In some instances it may be desirable to encase the electrode in an electrically communicating shield, e.g., gelatin.

In one embodiment, there are three electrodes, the sensing electrode, a reference electrode and a controlling electrode. The potential between the sensing electrode and the reference electrode can be varied by varying the potential applied to the controlling electrode with respect to the sensing electrode. The light emitting diode or other light source is powered with an external electronic circuit so as to emit light which may vary in a regular pattern, e.g., square-wave, sine-wave, etc., in intensity with time, resulting in a time dependent response of the sensing electrode, which can be detected by measuring the current through the controlling electrode required to maintain a constant potential between the sensing electrode and the reference electrode.

In this configuration the peak to peak amplitude of the periodically varying current through the controlling electrode varies as a function of the chemical environment at the sensing electrode and as a function of the potential applied between the sensing electrode and the controlling electrode. This configuration can be further simplified by shorting together the leads to the controlling and reference electrodes and removing the reference electrode from the circuit.

Desirably, the conducting polar medium with which the counterelectrode is in electrical communication, e.g., immersed, will have a small amount of a redox couple or electron transfer agent, since in some instances the presence of the agent enhances the stability of the observed signal. Conveniently, the concentration will be in the range of about 1 mM to 0.1M. Inorganic redox couples may be employed, such as $Fe^{+3}/Fe^{+2}$, $Cu^{+2}$, $Cu^{+1}$, and $Mn^{+3}/Mn^{+2}$, or the like, where the metal ions may be complexed with such ligands as cyano, ammonia, halo, etc. Usually, where a redox or charge transfer agent is employed, the electrolyte solutions for the two electrodes—sensing electrode and counterelectrode—will be separated by a salt bridge.

Turning now to FIG. 1, the semiconductor electrode 10 is positioned at the surface of an aqueous medium 12. Lead 13 and potentiostat 11, e.g., Model 363 Potentiostat/Galvenstat PAR (Princeton Applied Research), connect the semiconductor electrode 10, the reference electrode 14 and the controlling electrode 15. The potentiostat 11 supplies a polarizing current through the controlling electrode 15 and sensing electrode 10, which maintains a constant potential between the sensing electrode and the reference electrode 14. The current required to maintain a fixed potential between electrodes 10 and 14 is recorded as a voltage on meter output 16. An LED 32 is controlled by pulse circuit 34 to emit regular pulses of light at a predetermined frequency.

Another circuit which may be employed involves automatically varying the potential between the controlling and sensing electrodes so as to maintain a constant amplitude sinusoidal current through the controlling electrode in response to sinusoidal irradiation of the sensing electrode. Turning now to FIG. 2, the circuit has depicted a silicon wafer 42 which serves as the sensing electrode and a platinum electrode 43 which serves as the controlling electrode. (Resistors and capacitors will not be specifically mentioned, although depicted in the figure.) An operational amplifier 44 converts the current passing through the controlling and p-doped silicon semiconductor electrodes to a voltage and feeds the signal to a bandpass amplifier 46, which is comprised of three operational amplifiers 50, 52 and 54. The signal from the bandpass amplifier 46 is fed to the precision rectifier 56 which includes two operational amplifiers 60 and 62 as well as two diodes 64 and 66. A variable filter 70 is provided to smooth out the rectified signal and determine the response time of the circuit to changes in the chemical environment at the silicon electrode. A negative signal is fed to the controlling amplifier 72 which includes potentiometer 74 and operational amplifier 76. The controlling amplifier serves to control the potential at the platinum electrode 43. The negative signal fed to the controlling amplifier 72 is related to the amplitude of the alternating current through the Pt and Si electrodes in response to the sinusoidal irradiation of the Si electrode 42. For recording, the signal from the controlling amplifier 72 is fed to a unity gain amplifier 74 which allows for control of the base value for the recorder. Thus, as different sites are irradiated with regular sine-wave pulses on the silicon wafer surface, the recorder will respond with the reading of the potential between the Pt and Si electrodes necessary to maintain a constant amplitude alternating current through the Pt and Si electrodes. This circuit is referred to as CAM for constant amplitude module. Circuitry not shown provides for sinusoidal light irradiation of the wafer in accordance with a predetermined schedule.

A third general circuit which may be employed involves automatically varying the peak to peak amplitude of the LED output so as to maintain a constant photoresponse of the sensing electrode at a constant potential between the sensing and controlling electrodes. In this configuration, the detected signal which is sensitive to the environment at the sensing electrode is the peak to peak current passing through the LED.

Another circuit which may be employed allows for operation in either one of two modes. In one mode the potential between the controlling and sensing electrodes is maintained constant and the amplitude of the sinusoidal current through the sensing electrode in response to sinusoidal illumination of the sensing electrode is used as a monitor of the environment of the sensing electrode at the site of illumination. This is referred to as the CP mode. In a second mode the circuit automatically varies the potential between the controlling and sensing electrodes so as to maintain a constant amplitude sinusoidal current through the sensing electrode. In this configuration the potential between the controlling and sensing electrodes is used as a monitor of the sensing electrode at the site of illumination. This is referred to as the CAM mode.

The above-described circuit is depicted in FIG. 7, which is a modification of the circuit of FIG. 2. In this circuit, the signal from the bandpass amplifier 46 is fed to a phase sensitive detector 150 comprised of operational amplifier 152 and transistor 158. The operational amplifiers may be Fairchild A741 amplifers and the transistor is a N-channel silicon FET (Radio Shack 276-2035). A variable filter 154 smooths out the rectified signal from the phase sensitive detector 150 and serves to determine the response time of the circuit to changes in the chemical environment at the silicon electrode. In the CAM mode a negative signal is fed to the controlling amplifier 156 which includes potentiometer 160 and operational amplifier 162. Potentiometer 160 selects the amplitude of the AC signal that is to be maintained constant. The controlling amplifier 156 serves to control the potential at the platinum electrode 43, analogous to the controlling amplifier 72 of FIG. 2, with a unity gain amplifier 164 having its counterpart in amplifier 74. The series diodes 166 limit the bias potential to a maximum of 1.5 V from the platinum to silicon electrodes. The double pole double throw switch 170 serves to select the mode of operation of the circuit (e.g., CAM or CP).

In the CP mode a negative signal from the phase sensitive detector is fed to amplifier 164 such that this amplifier works in the inverting mode and the output to the recorder is a signal proportional to the amplitude of the sinusoidal current through the platinum and silicon electrodes. The controlling amplifier 156 maintains a constant potential between the platinum and silicon electrodes. In both modes, the integrated circuit IC1 172 produces simultaneously 800 Hz sine waves and square waves. The square waves at pin 9 174 are fed to the transistor Q2 158 to provide a reference signal to the phase sensitive detector. Sine waves from pin 2 176 are fed to a variable phase shifter 180 which includes operational amplifier 182.

The phase shifted signal is capacitively coupled to the LED driver and LED 192 comprised of operational amplifier 184 and transistor Q1 186 and LED 188. This LED driver provides for varying the light output of the LED in a sinusoidal manner with an adjustable DC intensity value.

In certain cases it is desirable to monitor the DC component of the current passing through the silicon electrode under conditions where the silicon electrode is either dark or illuminated by a non-modulated light source. In this configuration, the circuit is operated in the CP mode and the output of operational amplifier A1 190 is filtered to remove the AC component of the signal and the resulting voltage is fed to a recorder. The voltage to the recorder is thus porportional to the DC component of the current through the silicon electrode.

FIG. 3 shows a cross-section of an exemplary device having silicon wafer 80 connected to a circuit by wire 82 and mounted in container 84. Container 84 has a plurality of compartments 86 in which different assay samples are present. The compartment walls 88 would generally be of about 0.5 to 5 mm in thickness. As a reaction proceeds in each of the compartments, particularly where the reaction occurs adjacent the wafer surface, a product is produced which diffuses to the wafer surface 90. For example, in the case of a redox reaction, the redox products produced in the compartment migrate to the surface 90 and affect the photoresponse of the surface, either by reacting or creating a surface potential. In this manner, there is relatively little interference between the signals obtained from the various sites on the wafer surface 90 associated with an individual compartment 86. A transparent or semitransparent window 93 is separated from the silicon surface 90 by means of the supports 94. A small gap 95 is present between the surface 90 and the walls 88, so that the fluid can communicate between the compartments and provide for electrical communication between the silicon electrode 80 and platinum electrodes 97. The compartments 99 will be unaffected by changes in compartments 86, so as to maintain the solution composition substantially constant during the assay. An array of LEDs 92 provide for sequential illumination through compartments 86 to an associated site on the surface 90. The signal is read in association with the period of illumination.

In FIG. 4 is a partially broken away diagrammatic view looking downwardly on a device employing a plurality of channels. A housing 100 has a plurality of channels 102 having an inlet manifold 104 and an outlet manifold 106. A single reference electrode 108 is provided as well as a plurality of controlling counterelectrodes 110 deposited on the inner surface of the window 111. A plurality of inlet ports 112 associated with each of the channels is provided for introduction of the sample into a particular channel. The sample mixes with the assay medium from manifold 104 and the mixture proceeds through a channel 102. The base of the channel is a photoresponsive electrode 114. An air bubble may be introduced after the sample to separate the sample mixture from the following fluid. An LED array is provided, which is not shown, which illuminates each of the channels along its length, so that one or more sites in each channel 102 can be irradiated. A photoresponsive electrode 114 is in contact with the sample assay medium streams passing through channels 102 and filling the channels so as to be in contact with the counterelectrodes 108 and 110.

In this mode, one could employ a homogeneous assay technique employing an enzyme which catalyzes the reaction resulting in a change in redox potential of the assay medium. The rate of the reaction in each channel can be determined by taking sequential readings as a function of time at the same or different points. The rate of reaction can be determined by making sequential readings as the assay medium traverses the channel at different points along the channel. Thus, the rate of change of enzymatic activity in each channel can be determined and related to the concentration of analyte in the sample assay medium. The continuous flow of assay medium through the channel can serve to wash the channel and restore the channel for the next determination. Alternatively, by employing various valves one can alternate medium with wash solution, so as to restore the channel to its original state.

FIG. 5 is a diagrammatic view of a photoresponsive surface having a plurality of sites which are insulated one from another, but connected to a common bus and having independent compartments for the assay medium. The device has a container 120 which is shown as having only one line of photoresponsive semiconductors 122. The photoresponsive semiconductors are in electrical contact with a common bus 124, connected to lead 126 for connection to an appropriate circuit. A plurality of tubes 130 connected to inlets 132 provide for introduction of solutions into the compartments 134. Each of the compartments is separated by dividers 136. The tubes 130 have three-way valves 140 so that the wash solutions or other common solutions may be introduced or removed by means of inlet port 142. By appropriate manipulation of the valves 140, the same solution may be introduced or removed from each of the compartments simultaneously, assuring uniformity. Individual sample inlets 144 are provided for each compartment, so that the sample solution is directly introduced into a compartment 134 without contamination from other samples. A common counterelectrode 146 is employed and introduced at a plurality of sites to provide for an average value. These electrodes are connected to the circuit, not shown, to which the common bus is connected. An LED array 150 is provided having individual LEDs 152 which can be controlled to sequentially illuminate the compartments in accordance with a predetermined schedule, so that the observed signal can be related to a specific compartment. Each of the photoresponsive devices 122 is coated with a specific binding layer indicated by the dark line 154. For the purposes of the following example, the layer would be a saccharide layer for which a specific lectin was available.

An assay could be carried out as follows: Using the manifold 156 the valves 140 would be arranged so that a solution containing an enzyme, such as cholesterol esterase conjugated to lectin could be simultaneously introduced into each of the compartments through inlets 132. After a sufficient time for incubation the solution would be withdrawn through inlets 132 and each of the compartments washed with an appropriately buffered wash solution. Individual sample solutions would be prepared containing an unknown sample or a standard, antibody to an analyte, e.g., morphine, a morphine conjugate to a cholesterol esterase inhibitor, cholesterol oxidase, horseradish peroxidase and methylene blue, as an electron transfer agent. Also included would be a cholesterol esterase substrate and the solution buffered to pH 6.7. Each of the compartments would then be partially filled with the buffered solution, whereupon introduction of the sample through sample inlets 144 and inlets 132 the compartments would overflow, so that there would be uniform electrical contact with the counter electrodes 146.

The hydrolysis of cholesterol ester results in production of cholesterol, which is oxidized to produce $H_2O_2$, which oxidizes the methylene blue in a reaction catalyzed by the horseradish peroxidase. The methylene blue would modulate the signal upon irradiation of the medium adjacent to the photoresponsive surface. The amount of enzyme which is inhibited would be directly proportional to the amount of analyte in the sample, since enzyme inhibitor conjugate bound to antibody to analyte would be inactive in inhibiting the enzyme. After sufficient time for reaction to occur to obtain a detectable signal at the concentration range of interest, the compartments would be sequentially irradiated and the signals detected by means of the circuit, not shown. After a sufficient time when one or more readings would have been made, the assay determination would be terminated by withdrawing the solutions from each of the compartments through inlets 132 and inlet port 142 by turning valves 134 to connect each of the inlets 132 with the inlet port 142. After removal of the assay media and washing the compartments, a concentrated saccharide solution would then be introduced into each of the compartments repetitively, until all of the enzyme had been removed from the surface. The compartments would then be washed with a wash solution to remove all of the unbound saccharide, followed by introduction of the enzyme-lectin conjugate to restore the compartment to its original state for performing an assay.

FIG. 8 indicates an additional embodiment using a modified microtiter plate 200. The plate 200 has a plurality of wells 202 with assay medium 204 in each well 202. The plate 200 has a plurality of partitions 206 and a boron p-doped silicon wafer 210 to which is bonded electrical lead for connection to an appropriate circuit (not shown). An electrode container 214 supports a semi-solid electrically conducting lead 216 having a plurality of projections 220 which extend into the assay media 204. The semi-solid is substantially transparent to light and may be made by preparing a 1.5 to 3 weight percent agar saline solution in an appropriate mold which includes the container 214 and then removing a portion of the mold after the agar has hardened. Polymeric agents other than polysaccharides such as agar may be employed as thickening agents, such as polyvinyl acetate, particularly partially hydrolyzed, polyacrylates, or the like.

A plurality of light sources 222 are provided which are connected to a circuit (not shown) through lead 224, so that each of the light sources may be individually controlled as to timing and the nature of the signal, e.g., a constant continuous signal, pulsed signal, sinusoidal signal, etc.

A salt bridge 226 provides for electrical communication with electrolyte solution 230 in which counterelectrode 232, e.g., platinum, is immersed. The silicon electrode 210 and the platinum electrode 232 are connected through a circuit (not shown).

The following experiments were constructed to demonstrate the use of the device to monitor the presence of molecules capable of participating in redox reactions. Evidence is also presented showing that signals are modified specifically by chemical species adjacent to the illuminated site of the silicon wafer and that the presence or absence of similar species at adjacent but non-illuminated sites have negligible effect.

Except where indicated otherwise, the experiments described in the following paragraphs employed the CAM-controlled device together with a single photoresponsive semiconductor electrode having two fluid-filled, open-ended channels adjacent to its surface. The semiconductor electrode is a 2-inch diameter P111 7-14 ohm "Pen Prime" boron-doped silicon wafer soldered to a copper wire, with electrical contact effected by use of an indium-gallium mixture. To construct the channels, the wafer is fixed to an optically clear garnet wafer by means of three strips of tape having adhesive on both sides and a thickness of 70μ. This dimension is then the depth of the channels, the other dimensions being 0.5 cm width and 3 cm length. The exposed garnet surface is then covered by optically opaque black electrical tape, except at two 25 mm² sites. These two transparent sites are each adjacent to one of the two channels and also to one of two LEDs. This configuration allows for site-specific (and channel-specific) illumination of the opposing continuous silicon wafer surface. The semiconductor electrode is positioned in such a way that the two channels both dip a few millimeters into the same bath of 40-50 ml 0.1M phosphate buffer, pH 6.7-6.8. The platinum electrode is either placed in this same bath or in an adjacent bath containing 40-50 ml 0.1M phosphate buffer to which is preferably added $K_4[Fe(CN)_6]$ at 0.2 mM and $K_3[Fe(CN)_6]$ at 0.3 mM (approximately). In this latter mode, the bath containing the platinum electrode is connected to that containing the silicon electrode by means of a salt bridge of half-saturated KCl solution, solidified by 2% agar. The ionic redox couple facilitates reversibility of the platinum electrode, a feature which may be important to reduce drift and increase electrical stability for some applications.

In the mode described above, the applied potential is typically −600 mV to −1000 mV with the AC photoresponse fixed at a preselected value.

Construction of a multiplicity of channels or compartments adjacent to the wafer facilitates comparison of one or more "experimental" samples with one or more "reference" samples. Using the two-channel silicon wafer/garnet wafer device, described previously, it is possible to monitor both channels on an essentially continuous basis through alternate illumination of the two sites described previously. The photoresponse as modified by the reference sample may be automatically subtracted from that modified by the experimental sample by sinusoidally illuminating both channels continuously and 180° out of phase and recording the amplitude of the alternating current using the circuit shown in FIG. 1, optionally with the reference and controlling electrodes shorted together.

To demonstrate the use of the device for measuring the concentration of oxidizing (electron accepting) molecules and monitoring redox reactions, the following experiments were performed. Reversibility of the platinum electrode was facilitated as previously described and the silicon wafer/garnet wafer assembly (having two channels) was employed. A redox solution was prepared which was 0.033M $Fe(CN)_6^{-4}/Fe(CN)_6^{-3}$, 0.1M NaCl, 0.014M phosphate. The redox solution was introduced into channels of the device described above. A plot of mvolts applied potential versus the log of the $Fe^{+2}/Fe^{+3}$ concentration ratio was plotted and gave a straight line with a slope of 49 mV/unit (FIG. 7). The response generated at the illuminated site is modified by the redox solution in the channel adjacent to that site, with negligible interference produced by the solution with a different $Fe^{+2}/Fe^{+3}$ value added to the parallel non-illuminated channel.

In further experiments the substance methylene blue (MB) was used as an electron-transfer agent communicating with the silicon wafer. Unless stated otherwise, the MB was at 5 µg/ml and the diluent was phosphate-buffered saline for these experiments. When MB at 5 µg/ml is introduced into a channel of the silicon wafer/garnet wafer assembly a transient (~30 sec) applied potential signal of about −90 mV is recorded. If NADPH at 1 mg/ml has previously been mixed with the MB solution and left for about 5 min (in a sealed container which includes little air), the recorded transient signal is about −8 mV. Use of varying concentrations of NADPH has shown that measurement of NADPH concentration is possible by means of this technique.

It is also possible to measure the concentration of the enzyme, horseradish peroxidase (HRPO), by a similar technique. Using MB at 5 µg/ml and $H_2O_2$ at 0.15%, together with various concentrations of HRPO (0.005 to 50 µg/ml), applied potential signals which were maintained at high values for several minutes were recorded. In a typical experiment, the maintained signal measured at 1 min after addition of the reagents to the device was −80 mV and −470 mV, respectively, for HRPO at 0.005 and 50 µg/ml (with intermediate applied potential values obtained for intermediate HRPO concentrations). In contrast, in the absence of HRPO, MB+$H_2O_2$ produces a transient 30 sec signal characteristic of MB alone which decays to the baseline value by 1min after addition to the device.

If MB is added to milk, at a final concentration of 5 µg/ml, and the mixture introduced into the device, an elevated MB-dependent applied potential signal is obtained. The amplitude of this signal is significantly reduced by the presence of *E. coli* growing in the milk. This indicates that bacterial growth may be monitored by such a method. The milk had not changed pH, as monitored using a pH meter, indicating that the signal reduction was not caused by a pH change, but by chemical reduction of MB.

It is also possible to use a similar technique to measure the concentration of $H_2O_2$. In an experiment designed to illustrate this, MB and HRPO were used together, each at 5 µg/ml. Addition of $H_2O_2$ (at various concentrations) prior to introduction of the mixtures to the device, showed that the transient signal observed at 6 µM $H_2O_2$ (−150 mV) was about 50% greater than that observed in its absence (−90 mV). In the range 0–50 µM $H_2O_2$, transient signals are obtained with amplitudes which are approximately linear with $H_2O_2$ concentration.

A similar technique has been used to assay glucose. In this case, glucose (at various concentration) was introduced to the enzyme glucose oxidase (GO) at 5 µg/ml and left at room temperature for 40 min. At this time, MB and HRPO were added to give a final concentration of 5 µg/ml of each substance and the solutions were sequentially introduced into the device. With 1.55 µg/ml (~8 µM) glucose the transient applied voltage signal was about 50% greater than that observed in its absence.

As evidenced above, assays can be performed for the substrates of such enzymes as cholesterol oxidase, galactose oxidase, uricase, xanthine oxidase, etc., to a level of better than 10 µM, or the enzymes themselves may be the species assayed. While the enzymes indicated above are associated with $H_2O_2$ formation, other enzymes not involving the formation of $H_2O_2$ will also be assayable.

At applied potential values (from silicon to platinum) of more than 0.3 V, introduction of MB (in its oxidized form) results in a net flow of electrons from the silicon wafer to the MB, both when the wafer is illuminated and when it is not. At applied potential values (from silicon to platinum) of less than 0.3 V, net electron flow is only detected upon illumination of the wafer at a site adjacent to fluid containing MB. Therefore, when the circuitry is employed in the CP mode, at applied potential values (silicon to platinum) of less than 0.3 V, measurement of direct current, illumination of the wafer at different sites, permits site-specific determination of oxidized MB concentration. MB which has previously been chemically reduced by substances such as NADPH or NADH is no longer reducible by electrons from the silicon wafer. Direct current measured upon illumination of the wafer has been shown to be proportional to oxidized MB concentration for the range 0 to 125 µM, as shown in Table 1.

TABLE 1

| Concentration MB (µM) | Direct Current (nA) |
|---|---|
| 0 | 0 |
| 25 | 168 |
| 50 | 330 |
| 75 | 480 |
| 100 | 630 |
| 125 | 780 |

When using appropriate circuitry for any of the cited applications, the photosignal from the redox pair is channel specific. Different redox compositions in different channels can be determined on a single monolithic surface, essentially simultaneously. It is also possible to measure one property in one channel, e.g., redox, and a different property in a different channel, e.g., pH.

It is evident from the above results, that the subject devices and methods provide for an accurate, rapid and efficient method for measuring a wide variety of materials in a redox medium capable of modulating an electrical photoresponse. The subject device can be adapted to be used with liquids, gels and solid materials. The device can be used for measuring a large number of samples substantially simultaneously, employing rapid readouts, allowing for redundancy, so as to ensure accurate results, and providing for concomitant standardization of determinations. The method can be used with a static (non-flowing) medium or a dynamic (flowing) medium. In addition, the method can be used for the determination of rates. Various types of separation techniques can be monitored or analyzed, such as electrophoresis, Southern blots, plaque formation, or the like, where specific sites can be defined in accordance with variations in signals and position on a surface.

Although the foregoing invention has been described in some detail by way of illustration and example for purposes of clarity of understanding, it will be obvious that certain changes and modifications may be practiced within the scope of the appended claims.

What is claimed is:

1. A photoresponsive device for making at different sites a plurality of determinations of a redox substance capable of modifying an electrical signal resulting from irradiation of a photoresponsive element, said device comprising:
    a photoresponsive element having an irradiation receiving surface;
    irradiation means for irradiating at least two sites on said surface to provide distinguishable signals;
    a counterelectrode;
    means for polarizing said element with respect to said counterelectrode;
    first container means for retaining media in which said substance is to be determined in a photoresponsive modifying relationship to at least two sites;
    second container means for maintaining a first electrolyte in electrical communication with said photoresponsive element;
    third container means for maintaining a second electrolyte in electrical communication with said counterelectrode;
    means for providing electrical communication between electrolyte in said second and third container means without mixing of said first and second electrolytes; and
    means for measuring the electrical photoresponse during irradiation of a site.

2. A device according to claim 1, wherein said photoresponsive element is a monolithic doped silicon semiconductor wafer.

3. A device according to claim 1, including a clear sheet in close spaced apart parallel juxtaposition to said irradiation receiving surface.

4. A device according to claim 1, wherein said irradiation means is an LED array programmed to provide light pulses.

5. A device according to claim 1, wherein said container means is a plurality of channels, each of said channels associated with an irradiation site.

6. A device according to claim 1, wherein said container means is a plurality of compartments, each of said compartments associated with an irradiation site.

7. A device according to claim 1, wherein a portion of said element is coated with a lipid bilamellar layer for contact with said media.

8. A device according to claim 7, wherein said lipid bilamellar layer is coated on said irradiation receiving surface and has a specific binding pair member bound to said layer.

9. A method for substantially simultaneously determining a redox substance in a plurality of volumes of an electrically responsive medium, employing a photoresponsive element having a common lead through an electrical circuit to a counterelectrode, wherein said substance is capable of modulating the photoresponse of said element;
    said method comprising:
        directing said medium into photoresponsive modifying relationship with a photoresponsive surface of said element;
        maintaining electrical communication between said element and said counterelectrode through an electrically responsive fluid or gel;
        irradiating said surface at a plurality of sites in relation to individual volumes at different times in a predetermined sequence for defined periods of time at each of said sites; and
        determining by means of said circuit the presence of said substance in each of said volumes by the effect of said substance on the photoresponse resulting from said irradiation.

10. A method according to claim 9, wherein said circuit includes means for polarizing said element in relation to said counterelectrode and means for measuring the current necessary to restore the level of polarization during irradiation of said surface.

11. A method according to claim 9, wherein said circuit includes means for varying the light intensity in relation to said photoresponse.

12. A method according to claim 9, wherein said circuit includes means for fixing the potential between said photoresponsive element and counterelectrode and for fixing the intensity of said irradiation and determining the DC component of the photoresponse.

13. A method according to claim 9, wherein said substance is an inorganic ion.

14. A method according to claim 9, wherein said photoresponsive element is a monolithic doped semiconductor.

15. A method according to claim 9, wherein said volumes are portions of at least one stream.

16. A method according to claim 9, wherein each of said volumes is physically separated from the other volumes.

17. A method according to claim 9, wherein said substance is methylene blue, Meldola blue, or phenazine methosulfate.

18. A method according to claim 9, wherein said circuit maintains said element and counterelectrode at a predetermined potential difference and measures the current necessary to restore the potential difference upon irradiation of said surface.

19. A method according to claim 9, wherein said substance is a result of an enzymatic reaction.

20. A method according to claim 19, wherein said substance is reduced or oxidized indirectly through one or more intermediate compounds by the product of said enzyme.

21. A method according to claim 19, wherein said enzyme is an oxidoreductase.

22. A method according to claim 21, wherein said oxidoreductase is a peroxidase.

23. A method according to claim 21, wherein said enzyme is a dehydrogenase.

24. A method for determining the presence of an analyte in a sample, which analyte is a member of a first specific binding pair consisting of ligand and receptor, said method employing:
(a) a photoresponsive electrode having an irradiation surface;
(b) a counterelectrode;
(c) an electrical circuit connecting said photoresponsive electrodes and counterelectrode and maintaining said electrodes in a predetermined potential relationship;
(d) a binding surface for binding a member of a specific binding pair, which surface is said irradiation surface or a facing surface in close spaced apart juxtaposition to said irradiation surface; and
(e) specific binding means for specifically binding one of said members of said first specific binding pair to said binding surface;
said method comprising:
in an aqueous assay medium, combining components with said specific binding means, said assay components including a sample, a labeled specific binding pair member, which labeled specific binding pair member is a member of said first pair or capable of binding to, either directly or indirectly, a member of said first pair, wherein said label is a member of a system capable of modulating the electrical photoresponse of said photoresponsive electrode by means of a change in redox potential, and any additional members of said system;
irradiating a plurality of sites on said irradiation surface in relation to individual volumes of said combined components at different times in accordance with a predetermined schedule; and
determining the electrical photoresponse as modulated by said system by means of said circuit as indicative of the presence of said analyte in said sample.

25. A method according to claim 24, wherein said photoresponsive semiconductor is a doped monolithic silicon wafer.

26. A method according to claim 24, wherein said label is an enzyme.

27. A method according to claim 24, wherein said specific binding means is a second ligand and receptor.

28. A method according to claim 27, wherein said second ligand and receptor are a saccharide and a lectin.

29. A method according to claim 27, wherein said second ligand and receptor are a ligand and a natural receptor or antibody.

30. A method for determining the presence of an enzyme substrate in a medium, wherein the product of said substrate results in the production of a product, capable of producing either directly or indirectly a detectable redox potential, said method employing:
(a) a photoresponsive semiconductor electrode having an irradiation surface;
(b) at least one counterelectrode;
(c) an electrical circuit connecting said photoresponsive electrode and counterelectrode and maintaining said electrodes in a predetermined potential relationship;
(d) a binding surface for binding said enzyme at a plurality of sites;
said method comprising:

contacting said enzyme at each of said sites with an aqueous medium containing said substrate and any additional components necessary for the enzymatic catalyzed reaction;
irradiating said sites on said irradiation surface at different times in accordance with a predetermined schedule; and
determining the electrical photoresponse as modified by said system by means of said circuit as a measure of the amount of said substrate present.

31. A method according to claim 30, wherein said enzyme is horseradish peroxidase.

32. A method according to claim 30, wherein said enzyme is glucose oxidase.

33. A method for determining the presence of one or more microorganisms in a medium, said method employing:
(a) a photoresponsive electrode having an irradiation surface having a plurality of sites;
(b) at least one counterelectrode;
(c) an electrical circuit connecting said photoresponsive electrode and counterelectrode and maintaining said electrodes in a predetermined potential relationship;
said method comprising:
contacting said medium at each of said sites under conditions where said microorganism remains viable and produces at least one metabolic product capable of modulating the photoresponsive of said photoresponsive electrode by means of a change in the detectable redox potential of said medium;
irradiating said sites on said irradiation surface at different times in accordance with a predetermined schedule; and
determining the electrical photoresponse as modified by said metabolic product by means of said circuit as an indication of the presence of a microorganism.

34. A method according to claim 33, wherein said microorganism is bound by a specific receptor in juxtaposition to said site.

35. A method for detecting the presence of an analyte in a medium, said method employing:
(a) a photoresponsive electrode having an irradiation surface having a plurality of sites;
(b) at least one counterelectrode;
(c) an electrical circuit connecting said photoresponsive electrode and counterelectrode and maintaining said electrodes in a predetermined potential relationship;
said method comprising:
contacting said medium at each of said sites, wherein said medium contains horseradish peroxidase, hydrogen peroxide and methylene blue, and the amount of horseradish peroxidase in said medium is related to the amount of analyte in said medium, said horseradish peroxidase catalyzing the oxidation of methylene blue;
irradiating said sites on said irradiation surface at different times in accordance with a predetermined schedule; and
determining the electrical photoresponse as a result of the reaction of the methylene blue at each of said sites.

* * * * *